United States Patent [19]

Totani et al.

[11] Patent Number: 4,968,826

[45] Date of Patent: Nov. 6, 1990

[54] PLATINUM COMPLEXES AND ANTITUMOR AGENTS CONTAINING THEM AS AN ACTIVE INGREDIENT

[75] Inventors: Tetsushi Totani; Osamu Shiratori; Yoshihiro Muraoka, all of Hyogo, Japan

[73] Assignee: Shionogi & Co., Ltd., Osaka, Japan

[21] Appl. No.: 495,169

[22] Filed: Mar. 16, 1990

[30] Foreign Application Priority Data

Mar. 30, 1989 [JP] Japan ................................. 1-80917

[51] Int. Cl.$^5$ .............................................. C07F 15/00
[52] U.S. Cl. .................................... 556/137; 556/136; 549/211; 549/212
[58] Field of Search ................ 556/136, 137; 514/492; 549/211, 210, 212, 206

[56] References Cited

U.S. PATENT DOCUMENTS 4,760,156  7/1988  Heffernan et al. ................... 556/136
4,808,730  2/1989  Bitha et al. ......................... 549/211

Primary Examiner—Arthur C. Prescott
Attorney, Agent, or Firm—Birch, Stewart, Kolasch & Birch

[57] ABSTRACT

Novel platinum complexes of the formula:

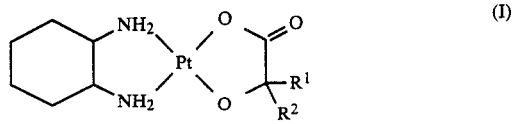

(I)

wherein $R^1$ and $R^2$ each identically of differently is lower alkyl, or $R^1$ and $R^2$ taken together form —(CH$_2$)$_m$—, and m is an integer from 2 to 5, and antitumor agents comprising the compound (I), which are effective against cisplatin-resistant ascitic murine leukemia, murine leukemia, and solid tumor, with slight hemotoxicity and nephrotoxicity.

10 Claims, No Drawings

PLATINUM COMPLEXES AND ANTITUMOR AGENTS CONTAINING THEM AS AN ACTIVE INGREDIENT

BACKGROUND OF THE INVENTION

1. Field of the Invention

The present invention relates to novel platinum complexes and antitumor agents containing them as an active ingredient.

2. Prior Art

Since platinum complexes were found to have antitumor activities, cisplatin (CDDP, Bristol-Meyers Co.), carboplatin (Bristol-Myers Co.), and many kinds of related compounds have been studied. Noticing antitumor activities of platinum complexes before now, the present inventors have diligently continued the research of such compounds. As a result, the present inventors have already disclosed glycolate platinum complexes (U.S. Pat. No. 4,560,781) and cis-diammineglycolate platinum (U.S. Pat. No. 4,575,550), and proved their utility. These achievements were also published in M. Nicolini (ed.) "Platinum and Other Metal Coordination Compounds in Cancer Chemotherapy", 744–748, Boston, Martinus Ni jhoff (1988).

SUMMARY OF THE INVENTION

The compounds of this invention show excellent antitumor activity against CDDP-resistant tumor cells. These compounds are effective not only in recurrent cases after recovering remission by CDDP treatment, but also in the treatment of many cases of other malignant tumors. Because the compounds of the invention show slight marrow suppression and hemotoxicity, they may be broadly used wither alone or in combination with other drugs without cumulative myelosuppression. In addition, the compounds of the present invention show no sign of nephrotoxicity.

DETAILED DESCRIPTION

The present invention relates to compounds of the formula:

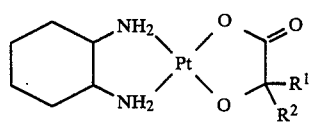

(wherein $R^1$ and $R^2$ each is identically or differently lower alkyl, or $R^1$ and $R^2$ taken together form —$(CH_2)_m$—, and m is an integer from 2 to 5).

In the present specification, the lower alkyl includes straightchain $C_1$–$C_4$ alkyl such as methyl, ethyl, propyl and butyl. Further, $R^1$ and $R^2$ may, taken together, form —$(CH_2)_m$—, and at this time the alkylene may be substituted by halogens such as F, Cl or Br, or lower alkyls such as methyl or ethyl.

Since the compounds of this invention show excellent antitumor activity against CDDP-resistant tumor cells, these compounds are effective not only for treatment of recurrent cases after remission by CDDP treatment, but also for treatment of most of other malignant tumors. Because the compounds of the invention show slight marrow suppression and hemotoxicity, they may be broadly used either alone or in combination with other drugs.

The compounds of the invention can be prepared by the following route, depending upon known methods [Wolf, W. et al, J. Pharm. Sci., 65, 315 (1976) and Totani, T. et al, Chem. Lett., 429 (1986)].

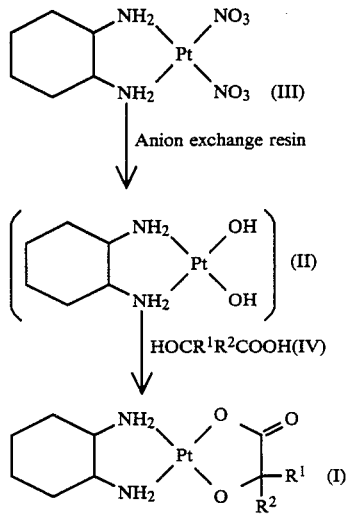

(wherein $R^1$ and $R^2$ each has the same meaning as defined above)

The dihydroxy-compound (II), in which two nitrato groups are replaced by hydroxy groups, can be prepared by passing aqueous solution of the compound (III) through a column filled with an anion exchange resin (OH—type) such as Diaion SA-10A. The compound (II) is dissociated in aqueous solution as shown below, showing alkalinity.

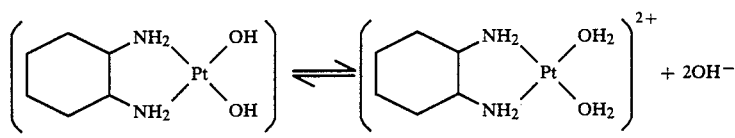

An aqueous solution of the compound (II) is allowed to react with one mol equivalent of the compound (IV), that is, 1-hydroxy-1-cycloalkanecarboxylic acid (IVa) or 2,2-dialkyl-2-hydroxyacetic acid (IVb) to give the desired compound (I). The ion exchange reaction from the compound (III) into the compound (II) proceeds quantitatively, so the compound (IV) may be used in one mol equivalent to the compound (III). In synthesizing the objective compound (I), in which $R^1$ and $R^2$ taken together form a cycloalkane ring, the desired cycloalkane ring is previously introduced into the compound (IV) and said compound (IV) is subjected to the next process for preparing the objective compound (I). This reaction is usually carried out at room temperature and terminates within 10 days, but if necessary, the reaction may be carried out at 50° to 70° C.

The compounds of the present invention (I) are active not only against customary solid tumors, but also against cisplatin-resistant mouse leukemia L1210 (L1210/CDDP). Another advantage of the compounds of the invention (I) is that they are almost free from marrow suppression or hemotoxicity at a dose high enough to exhibit such antitumor action.

The compounds of the present invention can be parenterally administered to humans or animals. For example, the compounds of the present invention can be dissolved in appropriate solvent for injection (e.g. distilled water for injection, physiological saline, 5% aqueous glucose solution, etc.) and administered intravenously or by way of intravenous drip.

The compounds of the present invention are preferably preserved in ampoules or vials in the form of crystals, powders, fine crystals or lyophilizates, and preferably dissolved in solution immediately before use. Stabilizers may previously be added in this case. For administration of the compound of the invention, it is recommended to repeat a cycle of administering parenterally 50 to 1500 mg/m$^2$ per adult in a single dosage or several divisions, and to withdraw during 2 to 4 weeks.

Presently preferred and practical embodiments of the present invention are illustratively shown in the following examples and experiments, but the present invention will not be limited by them at all.

EXAMPLE 1

(1R,2R-Diaminocyclohexane)[1-hydroxy-1-cyclopropanecarboxylato(2-)-O$^1$,O$^2$]platinum (II) (I-1)

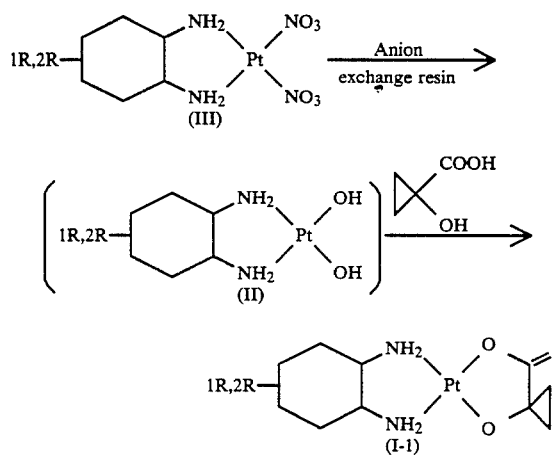

An aqueous solution of 955 mg (2.20 mmol) of dinitrato (1R,2R-diaminocyclohexane)platinum (III) in 30 ml of water is passed through a column filled with 20 ml of anion exchange resin (Diaion SA-10A, OH$^-$ type). To the resulting alkaline effluent is added a solution of 235.1 mg (2.23 mmol) of 1-hydroxy-1-cyclopropanecarboxylic acid in 2 ml of water, and the mixture is allowed to react at about 60° C. for 8 hours. The reaction solution is concentrated under reduced pressure, and the resulting crystals are filtered. The crystals are recrystallized from water to give 641.1 mg (yield; 69.6%) of the objective compound (I-1). mp. 195° C~ (decomp.)

Anal. Calcd. (%) for C$_{10}$H$_{18}$N$_2$O$_3$Pt.(H$_2$O)$_{0.5}$ :C, 28.71; H, 4.58; N, 6.70; Pt, 46.63. Found (%): C, 28.70; H, 4.60; N, 6.88; Pt, 46.65.

IR $\nu$ (Nujol): 3400 (b,m), 3180 (b, s), 3100 (b, s), 1630 (s), 1360 (s), 1260 (s), 1180 (m), 1130 (w), 1065 (m), 1030 (m), 990 (m), 905 (w), 830 (m), 740 (m) cm$^{-1}$.

$^1$H-NMR (D$_2$O, external standard TMS $\delta$): 1.42 (m, cyclopropane, 4 H), 1.50–2.26, 2.26–3.13 (b, m, cyclohexane, 10 H).

EXAMPLE 2

(1R,2R-Diaminocyclohexane)[1-hydroxy-1-cyclopentanecarboxylato(2-)-O$^1$,O$^2$]platinum (II) (I-2)

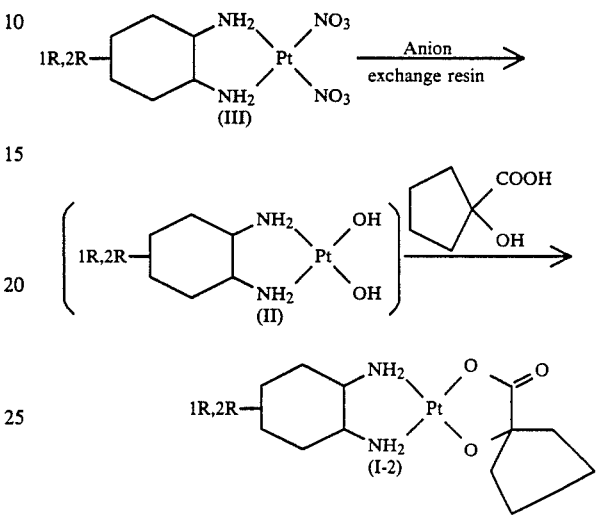

To an aqueous solution of the dihydroxy compound (II) obtained by treating 1.203 g (2.78 mmol) of the dinatrato compound (III) in the same manner as in Example 1, is added 363.4 mg (2.79 mmol) of 1-hydroxycyclopentanecarboxylic acid, and the mixture is reacted at 60° C. for 4 hours. The reaction solution is concentrated to dryness under reduced pressure, and the residue is dissolved in a small amount (5 to 6 ml) of methanol. It is subjected to silica gel column chromatography, and the eluate of Rf=0.60 (methanol) is collected. The resulting component is concentrated, the residue is mixed with acetone, and the resulting crystals are collected. The crystals are washed twice with acetone and dried under reduced pressure to give 876.7 mg (Yield: 72.1%) of the objective compound (I-2). · mp.: 215° C.~(decomp.).

Anal Calcd. (%) for C$_{12}$H$_{22}$N$_2$O$_3$Pt: :C, 32.95, H, 5.07; N, 6.40; Pt, 44.60. Found (%): C, 32.97; H, 5.20; N, 6.44; Pt, 43.72.

IR, $\nu$ (Nujol): 3400 (b, m), 3200 (b, s), 3100 (b, s) 1640 (vs), 1350 (s), 1320 (w), 1305 (w), 1175 (m), 1120 (w), 1070 (m), 1035 (m), 1020 (m), 955 (w), 925 (w), 840 (m) cm $^{-1}$.

$^1$H-NMR (D$_2$O, external standard TMS $\delta$), 1.33–3.02 (b, m cyclopentane+cyclohexane)

EXAMPLE 3

(1,2-Diaminocyclohexane)[1-hydroxy-1-cyclopentanecarboxylato(2-)-O$^1$,O$^2$]platinum (II) I-3

2.20 g (5.08 mmol) of the dinitrato (III), which was obtained from the starting 1,2-diaminocyclohexane (a mixture of cis and trans isomers. Tokyo Kasei) in a conventional manner, is treated in the same manner as in Example 2 to give 1.634 g (yield: 73.6%) of the objective compound (I-3) (a mixture of cis and trans isomers). mp. 228° C.~(decomp.).

Anal Calcd. (%) for $C_{12}H_{22}N_2O_3Pt$: : C, 32.95, H, 5.07; N, 6.40; Pt, 44.60. Found: C, 32.89; H, 5.07; N, 6.49; Pt, 44.57.

IR, $\nu$ (Nujol): 3420 (w), 3210 (m), 3118 (m), 1637 (vs), 1343 (s), 1313 (m), 1305 (sh), 1211 (w), 1111 (w), 1097 (w), 1062 (m), 1032 (w), 1013 (w), 984 (w), 947 (w), 919 (w), 855 (w), 837 (w) cm$^{-1}$.

$^1$H-NMR (D$_2$O, external standard TMS $\delta$): 1.33–3.73 (b, m cyclopentane+cyclohexane).

EXAMPLE 4

(1R,2R-Diaminocyclohexane)[2-hydroxy-2-methyl-butyrato(2-)-O$^1$, O$^2$-]platinum (II) (I-4)

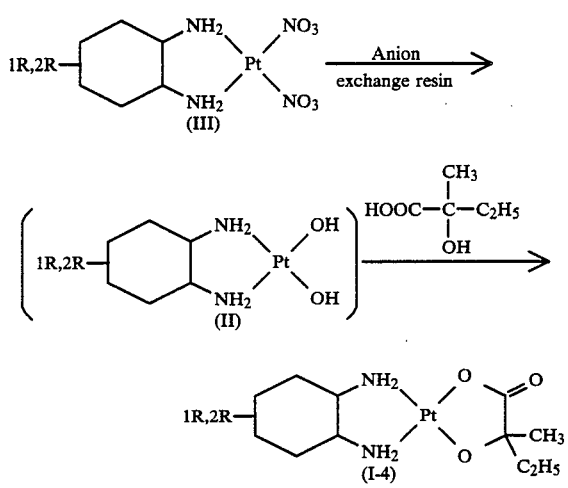

A solution of 4.59 mmol of the dinitrato (III) in water is treated in the same manner as in Example 1. An aqueous solution of the resulting dihydroxy compound (II) is mixed with 544.5 mg (4.61 mmol) of 2-hydroxy-2-methylbutyric acid, and the solution is heated at 60° to 63° C. for about 7 hours. The reaction mixture is concentrated under reduced pressure, and the residue is dissolved in methanol. The solution is subjected to silica gel column chromatography, and the eluate of Rf=0.57 (methanol) is collected. The solution is concentrated to about 2 ml and mixed with acetone to precipitate crystals, and the resulting crystals are collected. The crystals are washed twice with acetone and dried under reduced pressure to give 1.54 g (yield: 78.8%) of the objective compound (I-4) as white crystalline powder. mp. 240° C. ~ (decomp.)

Anal Calcd. (%) for $C_{11}H_{22}N_2O_3Pt$: C, 31.06; H, 5.21; N, 6.59; Pt, 45.86. Found (%): C, 31.18; H, 5.19; N, 6.28; Pt, 45.27.

IR, $\nu$ (Nujol): 3396 (b, m), 3204 (s), 3110 (s), 1639 (vs), 1341 (m), 1313 (w), 1261 (w), 1178 (m), 1131 (w), 1063 (w), 1032 (w), 926 (w), 829 (w), 664 (w) cm$^{-1}$.

$^1$H-NMR (D$_2$O, internal standard DSS $\delta$): 1.024, 1.039* (t, 3 H, —CH$_2$CH$_3$), 1.231, 1.230* (s, 3 H, —CH$_3$), 1.1–1.7 (m, 8 H, cyclohexane C$_3$, C$_6$-Hax, C$_4$, C$_5$-H$_2$, —CH$_2$CH$_3$), 2.04 (bm, 2 H, cyclohexane, C$_3$, H$_6$-Heq), 2.30 (bm, 2 H, cyclohexane, C$_1$, C$_2$-H) (*: symbol for geometrical isomer).

EXAMPLE 5

(1R,2R-Diaminocyclohexane)[2-ethyl-2-hydroxybutyrato(2-)-O$^1$,O$^2$]platinum (II) (I-5)

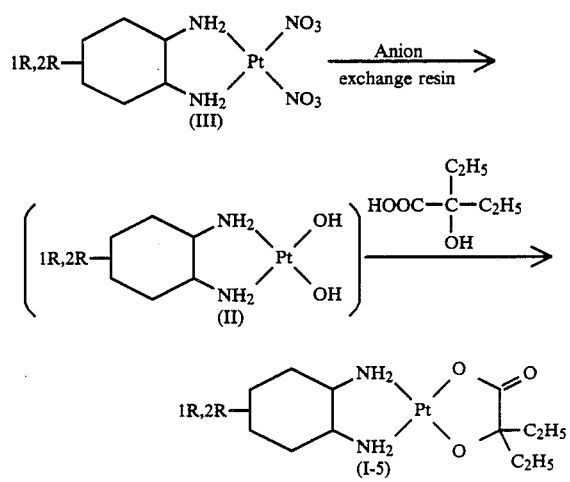

A solution of 4.59 mmol of the dinitrato (III) in water is treated in the same manner as in Example 1. An aqueous solution of the resulting dihydroxy compound (II) is mixed with 612.5 mg (4.63 mmol) of 2-ethyl-2-hydroxybutyric acid, and the solution is treated in the same manner as in Example 4 to collect the eluate of Rf=0.65 (methanol). The eluate is concentrated and the residue is cooled with ice. The precipitating pale yellow solid is collected by decantation, and dried at about 90° C. for 4 hours to give 1.158 g (yield: 57.4%) of the objective compound (I-5). mp. 220° C. ~ (decomp.).

Anal Calcd. (%) for $C_{12}H_{24}N_2O_3Pt$: :C, 32.80; H, 5.51; N, 6.37; Pt, 44.40. Found (%): C, 33.44; H, 5.71; N, 6.31; Pt, 44.03.

IR $\nu$ (Nujol): 3196 (m), 3104 (m), 2424 (vw), 1602 (vs), 1319 (m), 1277 (m), 1210 (vw), 1177 (m), 1157 (m), 1128 (w), 1063 (m), 1034 (w), 974 (s), 920 (w), 861 (vw), 840 (m), 794 (w), 742 (w), 670 (m), 569 (w) cm$^{-1}$.

$^1$H-NMR (D$_2$O, internal standard DSS, $\delta$): 0.973, 0.99 (t, 6 H, —CH$_2$CH$_3$×2), 1.05–1.63 (m, 10 H, cyclohexane, C$_5$, C$_4$-H$_2$,C$_3$, C$_6$-Hax, —CH$_2$CH$_3$×2), 2.045 (bm, 2 H, cyclohexane, C$_3$, C$_6$-Heq), 2.297 (bm, 2 H, cyclohexane, C$_1$, C$_2$-H).

EXAMPLE 6

(1R,2R-Diaminocyclohexane)[2-hydroxyisobutyrato(2-)-O$^1$,O$^2$]platinum (II) (I-6)

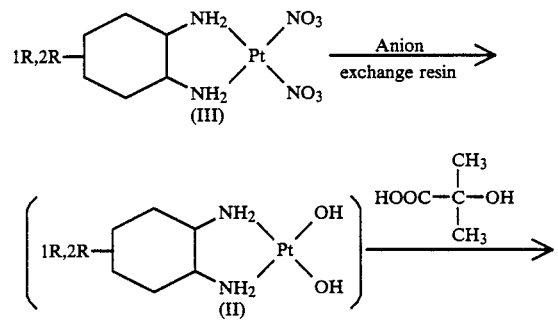

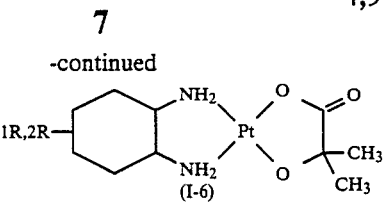

To an aqueous solution of 2.72 mmol of the dihydroxy compound (II) is added 283.2 mg (2.72 mmol) of 2-hydroxyisobutyric acid, and the resulting solution is treated in the same manner as in Example 4 to give 661.8 mg (Yield: 59.0%) as pale yellow crystals. mp. 240° C. ~ (decomp.)

Anal Calcd. (%) for $C_{10}H_{20}N_2O_3Pt(H_2O)_{0.5}$ :C, 28.57; H, 5.04 ; N, 6.66; Pt, 46.41. Found (%): C, 28.79; H, 4.99; N, 6.80; Pt, 46.52.

IR $\nu$ (Nujol): 3410 (b, m), 3272 (m), 3132 (m), 1617 (s), 1544 (w), 1332 (m), 1262 (w), 1195 (m), 1170 (w), 1156 (w), 1130 (w), 1065 (w), 1035 (w), 968 (m), 920 (w), 894 (w), 860 (w), 832 (m), 772 (w), 677 (m) cm$^{-1}$.

$^1$H-NMR (D$_2$O, internal standard DSS $\delta$): 1.297, 1.315 (s×2, 6 H, —CH$_3$×2), 1.05–1.70 (m, 6 H cyclohexane, C$_3$, C$_6$-Hax, C$_4$, C$_5$-H$_2$), 2.04 (bm, 2 H, cyclohexane, C$_3$H$_6$-Heq), 2.30 (bm, 2 H, cyclohexane, C$_1$, C$_2$-H).

EXAMPLE 7

(1R,2R-Diaminocyclohexane)[1-hydroxy-1-cyclohexanecarboxylato(2-)-O$^1$,O$^2$]platinum (II) (I-7)

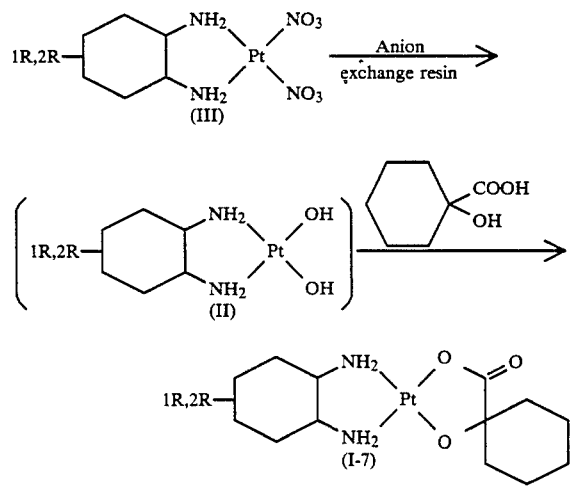

An aqueous solution of 8.33 mmol of dinitrato compound (III) is treated in the same manner as in Example 1 to give about 100 ml of an aqueous solution of dihydroxy compound (II). The solution is mixed with 1.2 g (8.34 mmol) of 1-hydroxy-1-cyclohexanecarboxylic acid, and the mixture is reacted at 60°-65° C. for 6 hours. The reaction mixture is concentrated to dryness under reduced pressure, and the resulting residue is dissolved in ethanol. It is subjected to silica gel column chromatography, and the eluate of Rf=0.59–0.60 (methanol) is collected. The eluate is recrystallized from ethanol to give 2.1 g (Yield: 50.6%) of the objective compound (I-7). mp. 240° C. ~ (decomp.)

Anal Calcd. (%) for $C_{13}H_{24}N_2O_3Pt \cdot C_2H_5OH$: :C, 36.21; H, 6.08; N, 5.63; Pt, 39.21. Found: C, 34.70; H, 5.99; N, 5.86; Pt, 39.13.

IR $\nu$ (Nujol): 3658 (w), 3356 (m), 3232 (s), 3200 (sh), 3124 (s), 1624 (vs), 1602 (sh), 1345 (m), 1305 (s), 1290 (s), 1269 (m), 1260 (m), 1222 (m), 1192 (w), 1165 (m), 1152 (m), 1126 (w), 1090 (w), 1066 (m), 1046 (m), 1031 (m), 980 (m), 932 (vw), 912 (vw), 882 (vw), 839 (w), 819 (w), 740 (m), 716 (w).

$^1$HNMR (D$_2$O, DSS, $\delta$): 1.02–1.64 (m, cyclohexanecarboxylato (OH)); 1.02–2.40 (m, 1R, 2R-cyclohexane, 10 H).

EXPERIMENT 1

Antitumor activities against murine leukemia cells (L1210) and cisplatin-resistant murine leukemia cells (L1210/CDDP):

(Test method)

Murine leukemia L1210 (or L1210/CDDP) ascitic cells (1×10$^5$ cells) (5×10$^5$ cells for L1210/CDDP) were intraperitoneally inoculated to BDF$_1$ mice (each group consisting 6~10 mice), and on the next day a predetermined amount of the test compound was intraperitoneally administered. 0.9% physiological saline was used as a solvent for injection.

(Test compounds)

A: (1R,2R-Diaminocyclohexane)[1-hydroxy-1-cyclopentanecarboxylato(2-)-O$^1$,O$^2$]platinum (II)

B: (1R,2R-Diaminocyclohexane)[1-hydroxy-1-cyclopropanecarboxylato(2-)-O$^1$,O$^2$]platinum (II)

C: (1R,2R-Diaminocylohexane)[2-hydroxy-2-methylbutyrato(2-)-O$^1$, O$^2$]platinum (II)

D: Cisplatin (control)

E: Carboplatin (control).

(Judging method)

From the average survival days (a) in each test group and those (b) of the non-treated control group, the increase of lifespan (ILS) was calculated according to the following formula.

$$ILS\ (\%) = \frac{(a) - (b)}{(b)} \times 100$$

As compared with the non-treated control group, the dose of achieving 30% ILS (ILS$_{30}$) and the dose of achieving the maximum ILS (ILS$_{max}$) were obtained, from which the chemotherapy index (CI) was calculated.

$$CI = \frac{ILS_{max}}{ILS_{30}}$$

The greater the CI value, the more effective the drug.

(Results)

The results are shown in Tables 1 to 4.

TABLE 1

| | Antitumor effects on L1210/CDDP | | | |
|---|---|---|---|---|
| Test compound | Dose (mg/kg) | Number of mice | ILS (%) | Number of mice surviving 30 days or longer |
| A | 0 | 10 | — | — |
| | 5 | 6 | 1 | — |
| | 10 | 6 | 5 | — |
| | 20 | 6 | >50 | 2 |
| | 40 | 6 | >56 | 2 |
| | 80 | 6 | >110 | 4 |
| | 160 | 7 | 1 | — |
| B | 0 | 9 | — | — |
| | 5 | 7 | 6 | — |
| | 10 | 7 | 14 | — |

TABLE 1-continued

| | Antitumor effects on L1210/CDDP | | | |
|---|---|---|---|---|
| Test compound | Dose (mg/kg) | Number of mice | ILS (%) | Number of mice surviving 30 days or longer |
| | 20 | 7 | 4 | — |
| | 40 | 7 | >93 | 3 |
| | 80 | 7 | >179 | 6 |
| | 160 | 7 | −16 | — |

TABLE 2

| Antitumor effects on L1210/CDDP and solubility in water | | | | |
|---|---|---|---|---|
| Test compound | ILS$_{30}$ (mg/kg) | ILS$_{max}$ (mg/kg) | CI | Solubility (mg/ml) |
| A | 14.5 | 80 | 5.5 | >500 |
| B | 24 | 80 | 3.3 | 30 |
| D | ineffective | | | 1.4 |
| E | ineffective | | | 16 |

TABLE 3

| | Antitumor effects on L1210 | | | |
|---|---|---|---|---|
| Test compound | Dose (mg/kg) | Number of mice | ILS (%) | Number of mice survived 30 days or longer |
| A | 0 | 10 | — | — |
| | 5 | 7 | 10 | — |
| | 10 | 7 | 16 | — |
| | 20 | 7 | 19 | — |
| | 40 | 7 | 37 | 1 |
| | 80 | 7 | >81 | 3 |
| | 160 | 7 | >168 | 1 |
| | 320 | 7 | 14 | — |
| B | 0 | 10 | — | — |
| | 10 | 7 | 10 | — |
| | 20 | 7 | 21 | — |
| | 40 | 7 | 22 | — |
| | 80 | 7 | 66 | — |
| | 160 | 7 | >83 | 2 |

TABLE 4

| | Antitumor effects on L1210 | | |
|---|---|---|---|
| Test compound | ILS$_{30}$ (mg/kg) | ILS$_{max}$ (mg/kg) | CI |
| A | 31 | 160 | 5.2 |
| B | 45 | 160 | 3.6 |
| D | 2.7 | 10 | 3.7 |

EXPERIMENT 2

Antitumor activity against Colon tumor 38:

(Test method)

A tumor segment of Colon tumor 38 was transplanted beneath the dorsal skin of BDF$_1$ mice (6 to 10 mice in each group), and the test compounds were intravenously administered on the next day and on the 8th day after the next day, respectively. As solvent for injection, 0.9% physiological saline was used.

(Test compounds)

Test Compounds A, C, D and E were same as those used in Experiment 1.

(Evaluation of the Effect)

The chemotherapy index (CI) was determined by the following formula, from the dose of 50% growth inhibition in the mean tumor size in each test group, as compared with that of the non-treated control group (ED$_{50}$), and the acute toxicity level (LD$_{50}$).

$$CI = \frac{LD_{50}}{ED_{50}}$$

The greater the CI value, the more effective the drug.

(Results)

TABLE 5

| Antitumor activities against Colon tumor 38 | | | |
|---|---|---|---|
| Test compound | ED$_{50}$ (mg/kg) | LD$_{50}$ (mg/kg) | CI |
| A | 164.9 | 452.5 | 2.7 |
| C | 106.2 | 452.5 | 4.3 |
| D | 18.3 | 31.1 | 1.7 |
| E | Ineffective | | |

EXPERIMENT 3

Influence against murine nucleated bone marrow cell count, megakaryocyte count and platelet count in peripheral blood:

(Test method)

After a single intravenous administration of test compounds to male CDF$_1$ mice (7 weeks old), hemotoxicity was investigated by counting the nucleated bone marrow cell in femora (NBMC), megakaryocyte (MEG) and platelet (PLT) in peripheral blood. Measuring timing was taken when the three indices reached the minimal value, namely 4 days after administration for NBMC, and 7 days after for MEG and PLT.

(Test compounds)

Test Compounds A, D and E were same as those used in Experiment 1.

(Results)

The results are shown in Table 6.

Changes in the counts of nucleated bone marrow cells (NBMC), megakaryocytes (MEG) and platelets (PLT) in peripheral blood induced by administration of the test compounds are shown as hemotoxicity, expressed as the ratio of the value of each index in the test group to that of the non-treated conrol group as a percentage.

The smaller the value, the greater the hemotoxicity.

TABLE 6

| Influence against murine nucleated bone marrow cells, megakaryocytes, and platelets in peripheral blood | | | | |
|---|---|---|---|---|

Hemotoxicity of test compound = $\frac{\text{Index in test group}}{\text{Index in non-treated control group}} \times 100(\%)$

| Test Compound | Dose (mg/kg) | Hemotoxicity | | |
|---|---|---|---|---|
| | | NBMC | MEG | PLT |
| A | 31.0 | 108 | 114 | 116 |
| | 62.0 (1/5 LD$_{90}$) | 87 | 91 | 108 |
| D | 2.25 | 86 | — | — |
| | 4.50 (1/3.5 LD$_{90}$) | 80 | 71 | 95 |
| | 9.00 | 48 | 71 | 74 |
| E | 30.0 (1/6 LD$_{90}$) | 78 | 60 | 89 |
| | 60.0 | 75 | 45 | 65 |
| | 120.0 | 28 | 8 | 35 |

EXPERIMENT 4

Evaluation of nephrotoxicity in mice:

(Test method)

After a single intravenous administration of Test Compound A to male $CDF_1$ mice (6 weeks old) at a rate of 160 or 320 mg/kg*, the levels of creatinine and urea nitrogen in plasma were measured. The mice were presented for pathological examination of kidneys four days after administration. (*: 320 mg/kg would be a lethal dose if the observation period was further extended.)

(Results)

The results were shown in Table 7.

TABLE 7

| | Evaluation of nephrotoxicity of Test Compound A | | | | | | |
|---|---|---|---|---|---|---|---|
| | | | Body weight (g) | | Creatinine | Urea nitrogen | Pathological findings of |
| Compound | Dose (mg/kg) | Number of mice | 0 day later | 4 day later | (mg/kg) | (mg/dl) | kidneys |
| A | 160 | 7 | 25.0 | 22.6 | 0.26 | 22.6 | Normal |
|   | 320 | 7 | 24.5 | 18.7 | 0.27 | 23.3 | Normal |
| Control group (normal saline) | — | 7 | 24.7 | 26.4 | 0.29 | 23.4 | Normal |

What is claimed is:

1. A compound of the formula:

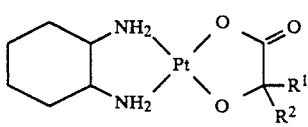
(I)

wherein $R^1$ and $R^2$ each identically or differently is lower alkyl, or $R^1$ and $R^2$ taken together form —$(CH_2)_m$—, and m is an integer from 2 to 5.

2. The compound claimed in claim 1, that is (1R,2R-diaminocyclohexane)[1-hydroxy-1-cyclopropanecarboxylato(2-)-$O^1,O^2$]platinum (II).

3. The compound claimed in claim 1, that is (1R,2R-diaminocyclohexane)[1-hydroxy-1-cyclopentanecarboxylato(2-)-$O^1,O^2$]platinum (II).

4. The compound claimed in claim 1, that is (1,2-diaminocyclohexane)[1-hydroxy-1-cyclopentanecarboxylato(2-)-$O^1,O^2$]platinum (II).

5. The compound claimed in claim 1, that is (1R,2R-diaminocyclohexane)[2-hydroxy-2-methylbutylato(2-)-$O^1,O^2$]platinum (II).

6. The compound claimed in claim 1, that is (1R,2R-diaminocyclohexane)[2-ethyl-2-hydroxybutylato(2-)-$O^1,O^2$]platinum (II).

7. The compound claimed in claim 1, that is (1R,2R-diaminocyclohexane)[2-hydroxyisobutylato(2-)-$O^1,O^2$]platinum (II).

8. The compound claimed in claim 1, that is (1R,2R-diaminocyclohexane)[1-hydroxy-1-cyclohexanecarboxylato(2-)-$O^1,O^2$]platinum (II).

9. An antitumor agent comprising a compound claimed in claim 1 as an active ingredient.

10. A process for preparing the compound claimed in claim 1 which comprises
reacting a compound (III) of the formula:

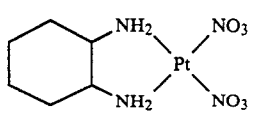
(II)

with an anion exchange resin to give a compound (II) of the formula:

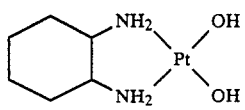
(III)

and reacting the compound (II) with a compound (IV) of the formula:

$$HOCR^1R^2COOH \qquad (IV)$$

wherein $R^1$ and $R^2$ each has the same meaning as defined above.

* * * * *